United States Patent [19]

Hickam et al.

[11] Patent Number: 4,472,355

[45] Date of Patent: Sep. 18, 1984

[54] CONCENTRATOR APPARATUS

[75] Inventors: William M. Hickam, Churchill Borough; William A. Byers, Penn Hills Township, Allegheny County, both of Pa.

[73] Assignee: Westinghouse Electric Corp., Pittsburgh, Pa.

[21] Appl. No.: 411,736

[22] Filed: Aug. 26, 1982

[51] Int. Cl.$^3$ ............................................ G01N 35/00
[52] U.S. Cl. ........................................ 422/62; 55/337; 60/657; 60/670; 159/1 R; 436/38
[58] Field of Search .................... 55/337, 204; 60/657, 60/646, 670; 73/61 R, 61.1 R, 61.3; 122/401; 159/1 R; 202/197; 203/3, 40; 210/512.2, 512.1, 787, 188; 422/62; 406/173; 436/38

[56] References Cited

U.S. PATENT DOCUMENTS 2,312,570  3/1943  Meier .................................. 122/401
4,222,997  9/1980  Beecher ............................. 203/12 X

OTHER PUBLICATIONS

Liebman et al., Automatic Concentrator Gas Chromatography System, Amer. Lab., vol. 7., No. 9, (Sep. 75), pp. 21-26.

Primary Examiner—Barry S. Richman
Assistant Examiner—Michael S. Gzybowski
Attorney, Agent, or Firm—D. Schron

[57] ABSTRACT

A liquid sample subject to inclusion of impurities is concentrated by a predetermined concentration factor selected by an operator, with the concentrated sample being thereafter provided to an analyzer so that a meaningful chemical analysis may be performed. A first pump delivers the sample to a liquid reservoir at a first rate and the liquid is boiled to provide a liquid-vapor mixture, with the liquid portion of the mixture being returned to the reservoir by means of a vapor separator. Another pump delivers the concentrated reservoir fluid to an analyzer at a second flowrate, with the ratio of the flowrate of the first pump to the second pump being equivalent to the desired concentration factor. In another embodiment, a faster response time is attained by first boiling the input sample and providing the liquid which is separated from the liquid-vapor mixture to a relatively small reservoir.

14 Claims, 8 Drawing Figures

CONCENTRATOR APPARATUS

BACKGROUND OF THE INVENTION

1. Field of the Invention

The invention in general relates to the field of chemical analysis, and particularly to apparatus which concentrates a liquid sample so that it may easily be chemically analyzed for detection of impurities.

2. Description of the Prior Art

The need for the precise monitoring of high purity liquids exists in many industries. Very low levels of impurities in the liquid can be extremely detrimental in the manufacture of, for example, semiconductors, pharmaceuticals, and in the power generation field, to name a few.

For example, in a steam turbine generator power plant, ultrahigh purity water is utilized in the generation of the steam which drives the turbines. The corrosive effects of impurities on turbines, boilers and other critical components in steam turbine power plants are well known and for this reason the circulating water for steam generation is maintained at an ultrahigh purity level measured in parts per billion, resulting in decreased outages and lower maintenance costs.

As part of the program for maintaining a high purity level of the water, it is necessary to collect representative samples of water or steam condensate from various locations in the steam turbine system so that they may be analyzed in order that corrective measures, if required, may be made.

Equipment exists for chemically analyzing the fluid utilized in various industrial processes, however, a problem exists in some plants, such as a steam turbine generator power plant, in that measurements must be made involving impurities measurable in parts per billion and even in parts per trillion. Direct constant monitoring of impurities at such low levels is extremely difficult and many commercial analyzers are not reliable to make measurements of impurity concentrations in this low range. To alleviate the problem, many processes use some sort of a concentrator to concentrate the sample provided for analysis.

A concentrator utilized in the monitoring of industrial process fluids, such as power plant water chemistry, should have high reliability and should be able to provide an output on a continuous flow basis with a reproducible concentration ratio of all chemical species of interest. Lower detection limits and increased sensitivity have been achieved through use of batchwise concentration techniques such as evaporation, liquid-liquid extraction, column ion exchange and reverse osmosis, however, these techniques either cannot be used with a continuous flow analyzer or are generally slow and laborious.

The present invention overcomes the deficiencies of the prior art apparatus and has the above-enumerated desired characteristics.

SUMMARY OF THE INVENTION

The continuous flow analytical concentrator of the present invention includes a fluid reservoir having an input sample line which has a first pump means for conducting sample liquid to the reservoir at a first flowrate, the sample being provided from some point in an industrial process or the like. An output concentrate line is in fluid communication with the reservoir and includes a second pump means for conducting liquid in the reservoir to an analyzer at a second flowrate which is compatible with the analyzer. The liquid in the reservoir is conducted to a boiler, the output of which is a liquid-vapor mixture which in turn is provided to a vapor separator which separates the vapor from the liquid-vapor mixture, with the vapor being exhausted through an output vapor line and the separated liquid being returned to the reservoir. The flowrates of the first and second pump means are accurately controlled to maintain a certain desired flowrate ratio, this ratio being equivalent to the amount of concentration, the concentration factor, imparted to the sample.

In another embodiment, a faster response time is achieved by first boiling the input sample and thereafter separating the vapor and liquid, with the vapor being exhausted out a vapor line and the liquid being provided to a fluid reservoir, with the output therefrom being provided to the analyzer.

DESCRIPTION OF THE PREFERRED EMBODIMENTS

Figure 1:
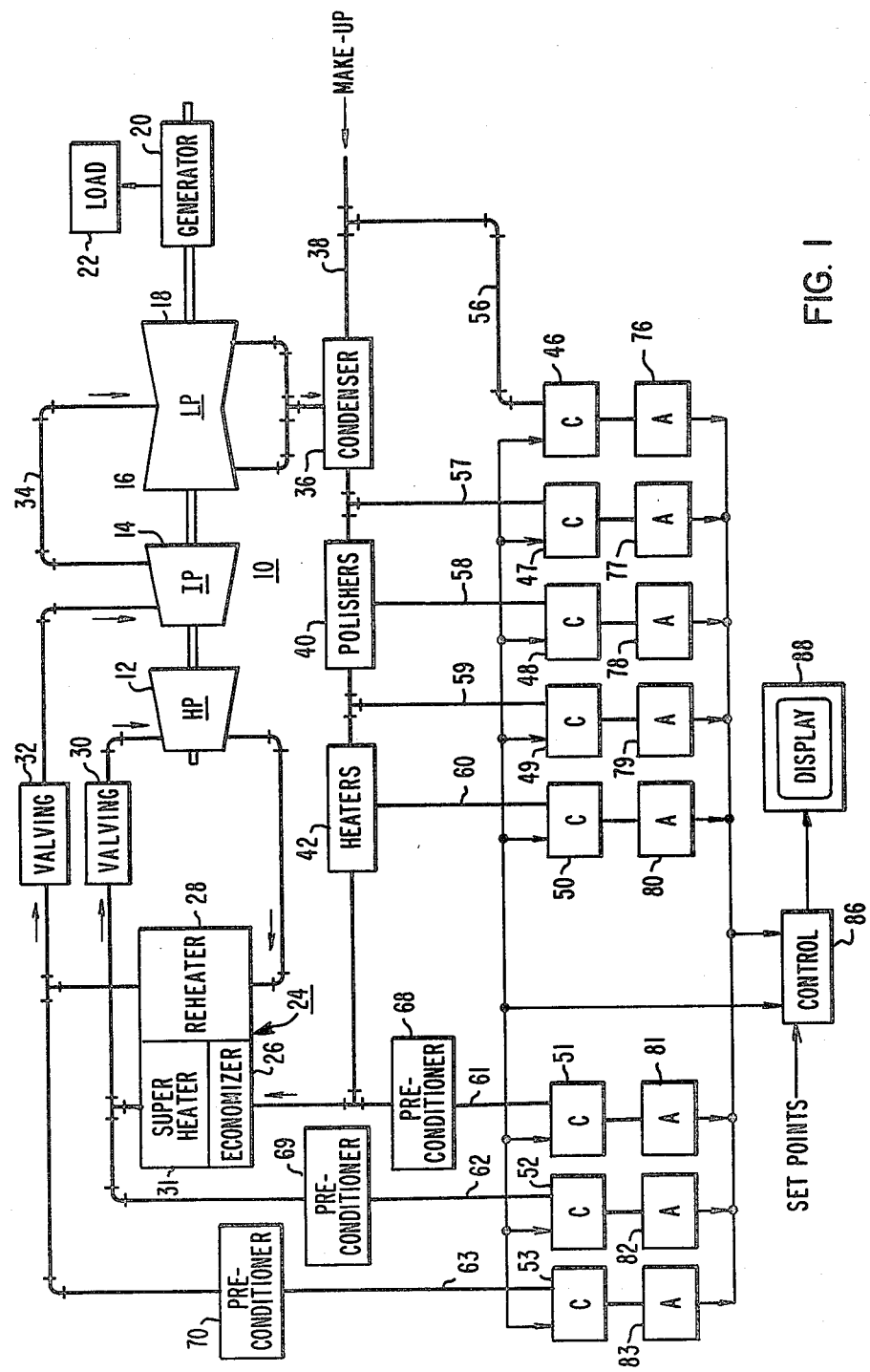
FIG. 1 illustrates a simplified diagram of a steam turbine generator power plant with steam/condensate chemical analysis equipment.

Although the invention is applicable to a variety of processes which require a continuous analysis of a fluid, it will be described by way of example with respect to a steam turbine generator power plant, and particularly a fossil fuel plant, a simplified block diagram of which is illustrated in FIG. 1.

The system includes a steam turbine arrangement 10 having a plurality of turbines in the form of a high pressure turbine 12, intermediate pressure turbine 14 and low pressure turbine 16, all of which are coupled to a common shaft 18 to drive an electrical generator 20 which supplies power to a load 22. A steam supply in the form of a boiler system 24 includes, by way of example, an input economizer section 26 and a reheater section 28. Boiler steam is provided to the turbine arrangement 10 through input valving 30 from superheater 31 and steam exiting the high pressure turbine 12 is reheated in reheater section 28 and provided to intermediate pressure turbine 14 through valving 32. Steam exiting the intermediate pressure turbine 14 is provided by way of crossover piping 34 to the low pressure turbine 16 from which the steam is exhausted into a conventional condenser 36.

Water in the condenser, along with any make-up water provided by fluid line 38, is recirculated back to the boiler after chemical treatment to maintain high purity. The chemical treatment may include a plurality of polishers 40 which basically are ion exchange units designed to remove impurities. After the chemical treatment, the water is heated by a series of heaters and returned (by pumps not illustrated) to the input economizer 26 of the boiler system 24.

In accordance with a good chemical monitoring program, fluid samples from various points in the system are extracted for continuous analysis for various known impurities. Numerous sample points may be provided throughout the system and a representative few are illustrated in FIG. 1. Thus by way of example, concentrator 46 receives a fluid sample from the make-up water via fluid line 56; concentrator 47 receives a fluid sample from the output of condenser 36 via fluid line 57; concentrator 48 receives a fluid sample from the polisher arrangement 40 via fluid line 58; concentrator 49 receives a fluid sample from the output of the polisher arrangement 40 via fluid line 59; concentrator 50 receives a fluid sample from the heater arrangement 42 via fluid line 60 and concentrators 51-53 receive fluid samples from the economizer 26, superheater 31 and reheater 28 via respective fluid lines 61-63 after the samples have been cooled by preconditioner 68 or have been converted to liquid form from its steam form by preconditioners 69 and 70.

Each concentrator 46-53 delivers its output concentrate to respective chemical analyzers 76-83 of the type which can analyze the fluid for one or more chemical characteristics.

The concentrator operation is under the direction of a central control 86 which receives predetermined operator-entered setpoints and which is also operable to output certain information for presentation on display 88, such information including the operator-entered values, and if desired, the results of the analysis from analyzers 76-83.

Figure 2:
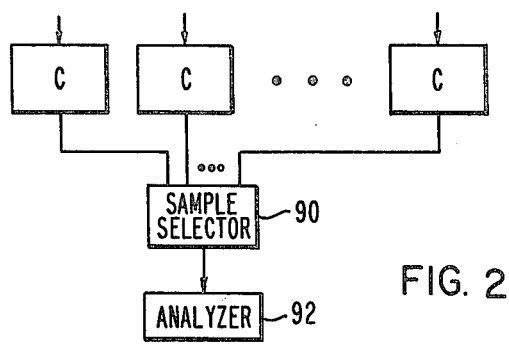
FIG. 2 illustrates an alternate view of a portion of the apparatus illustrated in FIG. 1.

For some operations it may be economically unfeasible to provide an analyzer for each concentrator. In such instance, an arrangement as illustrated in FIG. 2 may be utilized. In FIG. 2 a plurality of concentrators, designated with the letter C, provide their output concentrate to a sample selector means 90, which in one form may be a simple valving arrangment either manually operated or operated by the control 86 of FIG. 1 so as to provide one and only one concentrate output to the analyzer 92.

Figure 3:
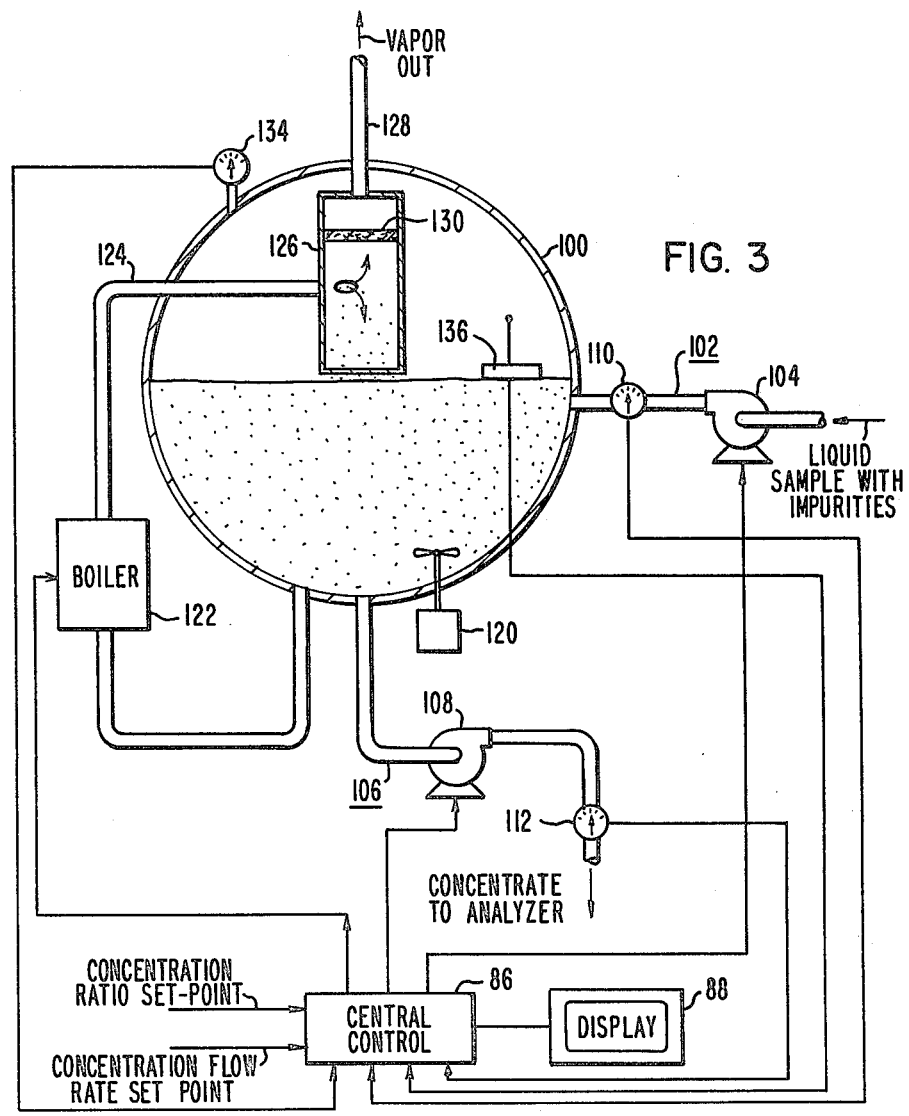
FIG. 3 illustrates one embodiment of the present invention.

A typical concentrator in accordance with one embodiment of the present invention is illustrated in FIG. 3 and includes a drum or fluid reservoir 100 operable to receive an input sample liquid which may be laden with impurities, via input sample line 102. Sample line 102 includes pump means in the form of a pump 104 which may be of the electrically controlled variety, the speed of which is governed by central control 86. An output concentrate line 106 for delivering a concentrated sample to an analyzer includes a second pump means in the form of an electrically operated pump 108 also under control of the central control 86. The flow transducers 110 and 112 are positioned relative to input sample line 102 and output condensate line 106 to provide flowrate indications of the input sample and output condensate as governed by pumps 104 and 108, respectively. The flowrate indications Q1 and Q2 are provided to central control 86 for maintaining a desired concentration of the input sample by a certain factor, herein termed the concentration factor CF, where $CF = Q1/Q2$.

A stirring mechanism 120 mixes the liquid in the reservoir 100, which liquid is converted to a liquid-vapor mixture by means such as boiler 122 which provides the liquid-vapor mixture via line 124 to a vapor separator 126. The vapor separator 126 is operative to separate the liquid from the vapor in the mixture and provide the liquid back to the reservoir 100 and to direct the vapor to the output vapor line 128. In the case of a steam turbine generator power plant, the liquid will be basically water and the vapor will be steam.

One type of separator 126 which may be utilized is a cyclone separator wherein the liquid-vapor mixture from line 124 enters the cylindrically shaped cyclone separator tangentially and begins to spin. The water is thrown to the walls of the separator by centrifugal force and exits by small holes in the separator wall and/or is pulled by gravity down the walls back to the reservoir. The less dense steam exits through steam line 128 and in order to provide for more complete separation, a screen separator 130 is provided near the top of the separator 126 so that small droplets of water which may impact on the screen will coalesce and fall back into the reservoir.

Two other sensors are provided, one being a pressure transducer 134 operative to provide an output signal indicative of the pressure within the reservoir 100 and the other being a level sensor 136 operative to provide an output signal indicative of the fluid in the reservoir, with both of these signals being used for control purposes by the central control 86.

A typical operation of the apparatus of FIG. 3 will be explained with additional reference to the flowchart illustrated in FIG. 4. Initially the concentrate flowrate Q2 and concentration ratio can be set manually or by the analyzer which the concentrator is serving. Initially the central control 86 compares the concentrate flowrate as indicated by the output of transducer 112 with the concentrate flowrate setpoint. If the concentrate flowrate is greater than the setpoint, as indicated by block 140, then the central control is operative to reduce the pumping speed of pump 108, as indicated by block 142. If the concentrate flowrate is less than the setpoint, as indicated by block 144, then the concentrate pump speed will be increased as indicated by block 146.

Assuming at this point that the concentrate flowrate is equal to the setpoint, that is, it is neither higher nor lower, than a check on the reservoir pressure is made by the central control examining the output signal from pressure transducer 134. If the pressure is low as compared to a predetermined operating pressure range, then block 148 indicates a correction is made by heating the boiler 122, as indicated by block 150. If the pressure is high as indicated by block 152, then the boiler is cooled as indicated at 154. The process continues and the results of this and further corrective actions which may be taken will be seen when the loop is again started at decision block 140. After the pressure check, the sample flowrate is checked with the desired flowrate as determined by the central control from the concentrate flowrate and concentration ratio setpoint ($Q1 = Q2 \times CF$). If the sample flowrate is less than indicated, then pump 104 is controlled to increase the speed, as indicated by block 158, and if the sample rate is greater than indicated, as determined by decision block 160, then the speed of pump 104 is decreased as indicated by block 162.

If the level of the fluid in reservoir 100 is too high, as indicated by block 164, then corrective action may be taken to increase the heat of the boiler and/or decrease the speed of pump 104, as indicated by blocks 166 and 167. The additional heat of the boiler will create a greater percentage of vapor so that less liquid is returned to the reservoir. The decrease of the speed of pump 104 will also insure that the level of the fluid will be returned to its operating range. If the level is too low, as indicated by block 168, then the reverse action may be taken to cool the boiler and increase pump speed as indicated by blocks 169 and 170. In effect, the level sensor may serve two functions, one of which is used as a check on the flow transducers 110 and 112 since if the pumps and boiler are properly adjusted, the level of the fluid in reservoir 100 should remain constant. Its other function is to make sure that the liquid vapor separator 126 is not flooded.

Figure 4:
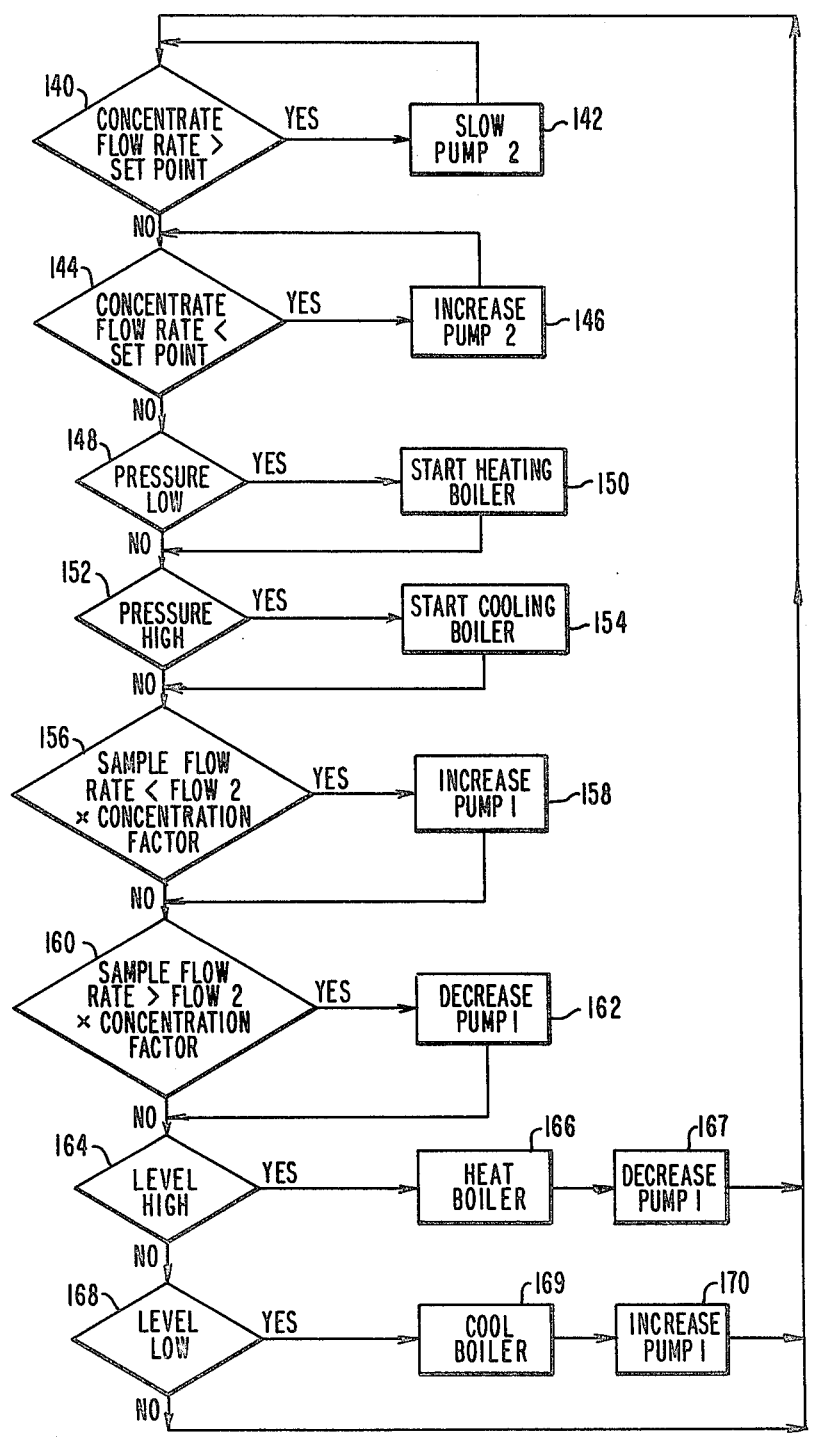
FIG. 4 is a flowchart illustrating the operation of the apparatus of FIG. 3.

The checks and any necessary control outputs, as indicated by the flowchart of FIG. 4, may be accomplished by any one of a variety of commercially available microcomputers which will continuously loop through the functions illustrated in FIG. 4.

The response time of the apparatus is dependent upon the concentration factor desired. By way of example, let it be assumed that the volume of liquid illustrated in the apparatus of FIG. 3 is 200 milliliters (ml). Let it be assumed that the concentrate flowrate is 10 ml per minute and that a concentration factor of 20 is desired. In such instance, the sample flowrate will be 200 ml per minute ($Q1 = Q2 \times CF$). Further by way of example let it be assumed that the apparatus is to respond to an increase of 5 ppb in sample impurity, for example, from 0 to 5 ppb. The response time of the apparatus is illustrated by curve 18 of FIG. 5 wherein time in hours is plotted on the horizontal axis and impurities in the concentrate in ppb is plotted on the vertical axis.

Since the impurity concentration was changed from 0 to 5 ppb, the final concentration in the output concentrate will contain impurities 20 times the amount in the sample, or 100 ppb. The time to reach an equilibrium of 100 ppb will be approximately 1½ hours. A relatively longer period of time will be expended to reach equilibrium with higher chosen concentration factors. For example, curve 182 shows that it will take approximately 4 hours for the concentrate to attain a value of 250 ppb in response to the initial 5 ppb change in the sample with a chosen concentration factor of 50. With a concentration factor of 100, curve 184 shows that it will take approximately 9 hours for the concentrate to attain a value of 500 ppb. Such time duration however may be necessary to adequately concentrate the sample liquid so that a precise reading may be provided by a particular analyzer, which under normal conditions would not be able to provide a meaningful output if the original sample were provided directly to it. Further in an industrial process such as encountered in a steam turbine generator power plant, the response times illustrated in FIG. 5 would be relatively nominal considering that the concentrator apparatus may be in continual use for days or months at a time.

Figure 6:
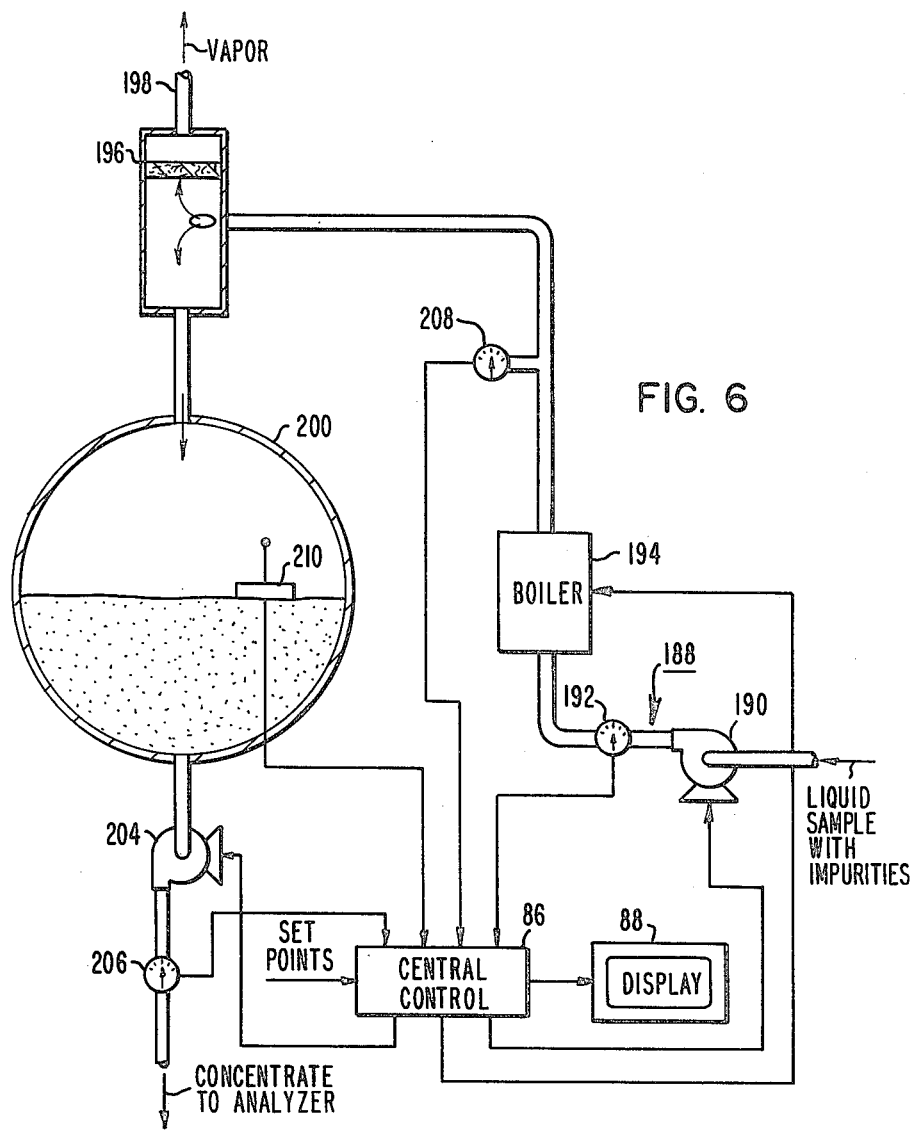
FIG. 6 illustrates another embodiment of the present invention.

If, however, the particular industrial process dictates that a faster response time be provided, then the embodiment of the apparatus illustrated in FIG. 6 may be utilized. The apparatus includes an input sample line 188 which includes a pump 190, the volumetric flowrate of which is sensed by a flow transducer 192 providing an output signal indicative of flowrate Q1. As opposed to the construction of the apparatus in FIG. 3, the apparatus of FIG. 6 includes a boiler 194 in the input line for converting the input sample liquid to an output vapor and liquid mixture which is provided to a vapor separator 196 which may be similar to that described in FIG. 3. The separated vapor exits through output vapor line 198 and the condensed liquid is directed to a fluid reservoir 200, which may be a fraction of the size of the fluid reservoir illustrated in FIG. 3. For example, if the fluid volume of reservoir 100 in FIG. 3 is 200 ml, the fluid volume of reservoir 200 in FIG. 6 may be 20 ml.

The concentrated liquid is delivered to the analyzer via the output concentrate line 202 which includes a pump 204, and a flow transducer 206 for providing an output signal indicative of Q2. Pressure and level sensors 208 and 210 are included for providing the central control 86 with boiler pressure and fluid level indications respectively.

Figure 5:
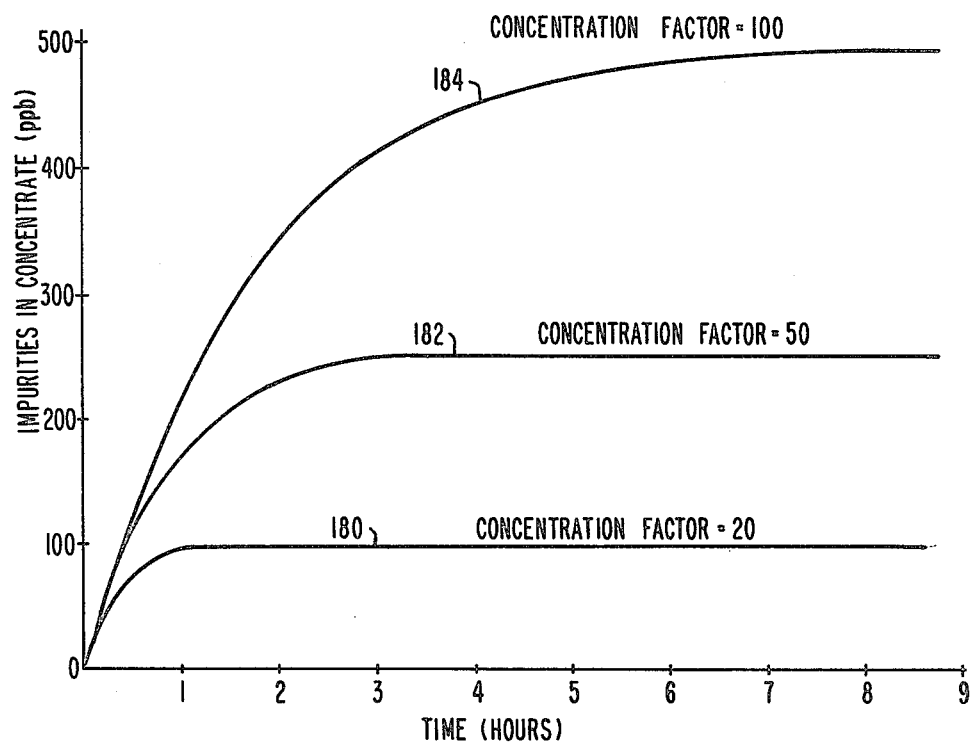
FIG. 5 shows curves illustrating the response time of the apparatus of FIG. 3.

The concentrator of FIG. 6 with its liquid to liquid-vapor conversion in the input line, coupled with a relatively small fluid reservoir allows for shorter response times than those illustrated by way of example in FIG. 5 utilizing a similar control strategy as described in FIG. 4. The faster response time however is achieved only through the maintaining of a very small amount of liquid in the reservoir at a substantially constant level, such operation therefore requiring a more precise and exacting control over the pump speeds and boiler operation.

Figure 8:
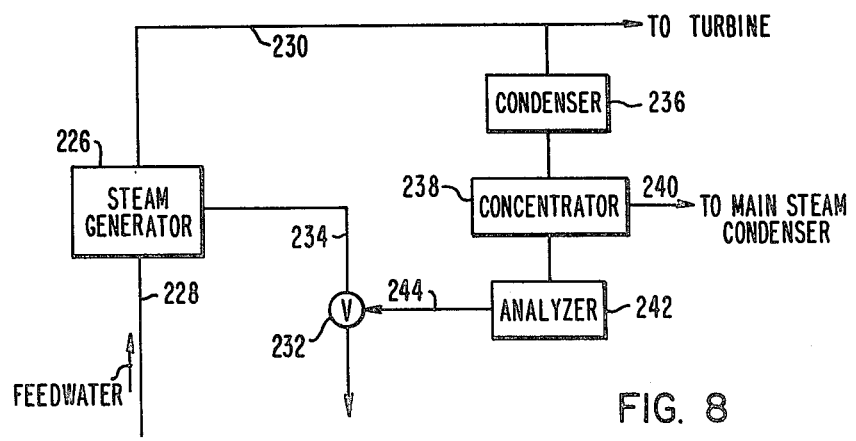
FIG. 8 is a block diagram illustrating the partial control of a main steam generator in a power plant.
Figure 7:
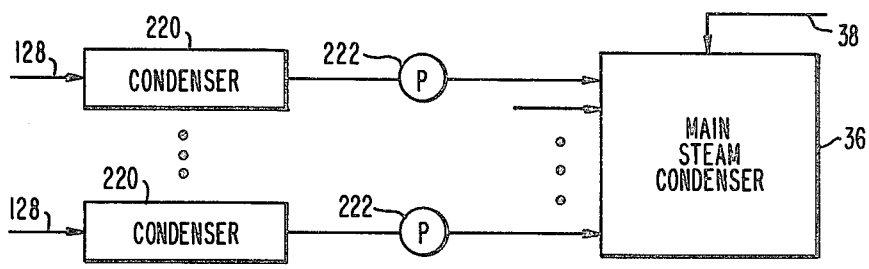
FIG. 7 illustrates components which may be connected to the vapor output lines of FIG. 3 and 6.

In the concentrator of FIG. 3, vapor is discharged through output vapor line 128. In a steam generator power plant, rather than discharging this high purity steam, it may be desirable to return it to the system. In such case, and as illustrated in FIG. 7, the steam in an output vapor line 128 may be provided to a condenser 220 for converting the steam into water which is then pumped back to the main steam condenser 36 by means of a pump 222. A similar arrangement may be provided for returning the vapor from output vapor line 198 of the concentrator embodiment of FIG. 6. The concentrators along with the analyzers constitute a steam chemistry monitoring system for prolonging the life and increasing the efficiency of steam turbine power plant apparatus and will maintain a constant desired concentration factor independent of the operational requirements of the particular plant. The concentrator together with the analyzer may also be utilitzed to control various operations, one of which is illustrated in FIG. 8.

A main steam supply in the form of steam generator 226 is operative to receive feedwater via line 228 to convert it to steam and supply it to the turbine via line 230. A control value 232 is positioned in blowdown line 234 generally utilized to remove some of the water in the steam generator should the concentration of one or more impurities therein attain an objectionable level. The steam supply in line 230 is tapped and converted to a liquid sample by means of condenser 236 where the liquid sample is then provided to concentrator 238 of the variety previously described. The output vapor concentrator 238 is delivered back to the main steam condenser via line 240 and the concentrate is provided to analyzer 242. By way of example, analyzer 242 may be a chloride analyzer which will provide an electrical output signal on electrical lead 244 to modulate the opening of valve 232 which may be of the electric or electro-hydraulic variety.

What we claim is:

1. A continuous flow analytical concentrator apparatus for concentrating a sample liquid by a predetermined concentration factor for delivery to an analyzer, comprising:

(A) means defining a fluid reservoir;

(B) analyzer means;
(C) an input sample line, including first pump means for conducting sample liquid to said reservoir means at a first flowrate Q1;
(D) an output concentrate line, including second pump means for conducting liquid in said reservoir means to said analyzer means at a second flowrate Q2 compatible with said analyzer means;
(E) an output vapor line;
(F) a vapor separator for separating vapor from a liquid-vapor mixture;
(G) boiler means;
(H) means for conducting liquid in said reservoir means to said boiler means wherein said liquid is converted to a liquid-vapor mixture;
(I) means for conducting said liquid-vapor mixture from said boiler means to said vapor separator, separated vapor therefrom being provided to said output vapor line and separated liquid therefrom being provided back to said reservoir means;
(J) means for generating a signal representative of a predetermined concentration factor; and
(K) control means for operating said first and second pump means to maintain a desired flowrate ratio Q1/Q2, said flowrate ratio being substantially equivalent to said predetermined concentration factor.

2. Apparatus according to claim 1 which includes:
(A) first flow transducer means positioned to sense the liquid flowrate Q1 in said input sample line and provide a corresponding output signal indicative thereof;
(B) second flow transducer means positioned to sense the liquid flowrate Q2 in said output concentrate line and provide a corresponding output signal indicative thereof; and
(C) said control means being responsive to said signals for operating at least one of said pump means to maintain a substantially constant ratio Q1/Q2.

3. Apparatus according to claim 2 which includes:
(A) pressure transducer means positioned to sense pressure within said reservoir means and provide a corresponding output signal indicative thereof;
(B) said control means being responsive to selected flow and pressure transducer signals to control operation of said boiler means.

4. Apparatus according to claim 2 which includes:
(A) level sensor means for sensing the level of the liquid in said reservoir means and providing an output signal indicative thereof;
(B) said control means being responsive to said level sensor signal to maintain said liquid level within predetermined limits.

5. Apparatus according to claim 1 which includes:
(A) a stirrer mechanism for mixing said liquid in said reservoir.

6. Apparatus according to claim 1 in which includes:
(A) said vapor separator is a cyclone separator.

7. Apparatus according to claim 6 which includes:
(A) screen baffle means in said cyclone separator to separate said liquid-vapor mixture.

8. Apparatus according to claim 2 which includes:
(A) display means for displaying the values of Q1 and Q2 and said predetermined concentration factor.

9. A continuous flow analytical concentrator for concentrating a sample liquid by a predetermined concentration factor for delivery to an analyzer, comprising:
(A) means defining a fluid reservoir;
(B) analyzer means;
(C) boiler means;
(D) an input sample line, including first pump means for conducting sample liquid to said boiler means at a first flowrate Q1 wherein said liquid is converted to a liquid-vapor mixture;
(E) an output concentrate line, including second pump means for conducting liquid in said reservoir means to said analyzer means at a second flowrate Q2 compatible with said analyzer means;
(F) an output vapor line;
(G) a vapor separator for separating vapor from said liquid-vapor mixture;
(H) means for conducting said liquid-vapor mixture from said boiler means to said vapor separator, separated vapor therefrom being provided to said output vapor line and separated liquid therefrom being provided to said reservoir means;
(I) means for generating a signal representative of a predetermined concentration factor; and
(J) control means for operating said first and second pump means to maintain a desired flowrate ratio Q1/Q2, said flowrate ratio being substantially equivalent to said predetermined concentration factor.

10. Apparatus according to claim 9 which includes:
(A) first flow transducer means positioned to sense the liquid flowrate Q1 in said input sample line and provide a corresponding output signal indicative thereof;
(B) second flow transducer means positioned to sense the liquid flowrate Q2 in said output concentrate line and provide a corresponding output signal indicative thereof;;and
(C) said control means being responsive to said signals for operating at least one of said pump means to maintain a substantially constant ratio Q1/Q2.

11. Apparatus according to claim 10 which includes:
(A) level sensor means for sensing the level of the liquid in said reservoir means and providing an output signal indicative thereof;
(B) said control means being responsive to said level sensor signal to maintain said liquid level within predetermined limits.

12. Apparatus according to claim 9 in which
(A) said vapor separator is a cyclone separator.

13. Apparatus according to claim 12 which includes:
(A) screen baffle means in said cyclone separator to separate said liquid-vapor mixture.

14. Apparatus according to claim 9 which includes:
(A) display means for displaying the values of Q1 and Q2 and said predetermined concentration factor.

* * * * *